United States Patent [19]

Agrawal et al.

[11] Patent Number: 5,243,078
[45] Date of Patent: Sep. 7, 1993

[54] PRODUCTION OF NONCYCLIC POLYALKYLENE POLYAMINES

[75] Inventors: Rakesh Agrawal, Allentown; John H. Frey, Alburtis, both of Pa.

[73] Assignee: Air Products and Chemicals, Inc., Allentown, Pa.

[21] Appl. No.: 370,473

[22] Filed: Jun. 23, 1989

[51] Int. Cl.[5] .......................................... C07C 209/64
[52] U.S. Cl. ................................................. 564/470
[58] Field of Search ....................... 564/479, 480, 470; 544/358, 402, 401; 502/63, 65, 66, 78

[56] References Cited

U.S. PATENT DOCUMENTS

| | | | |
|---|---|---|---|
| 3,506,400 | 4/1970 | Eberly, Jr. et al. | 23/182 |
| 4,036,881 | 7/1977 | Brennan et al. | 260/583 P |
| 4,394,524 | 7/1983 | Ford et al. | 564/479 |
| 4,503,253 | 3/1985 | Ford et al. | 564/479 |
| 4,547,591 | 10/1985 | Brennan et al. | 564/479 |
| 4,578,517 | 3/1986 | Johnson et al. | 564/479 |
| 4,582,904 | 4/1986 | Wells et al. | 544/178 |
| 4,582,936 | 4/1986 | Ashina et al. | 564/479 |
| 4,605,770 | 8/1986 | Ford et al. | 564/479 |

FOREIGN PATENT DOCUMENTS 0125616 11/1984 European Pat. Off. .

*Primary Examiner*—Allen J. Robinson
*Assistant Examiner*—P. O'Sullivan
*Attorney, Agent, or Firm*—Keith D. Gourley; James C. Simmons; William F. Marsh

[57] ABSTRACT

A process for selectively preparing predominantly noncyclic polyalkylene polyamines wherein one or more linear alkyleneamines are reacted in the presence of a mordenite catalyst under conditions sufficient to effect a disproportionation reaction. Preferably, the catalyst is prepared by treating the mordenite with an amount of a phosphorus-containing moiety sufficient to provide a catalyst which is impregnated with from about 0.01 to 15 wt % elemental phosphorus based upon the total weight of the impregnated mordenite catalyst. The process is especially useful in the production of diethylenetriamine wherein ethylenediamine is reacted in the presence of LZ-M-8 catalyst which has been treated with an amount of ammonium dihydrogen phosphate sufficient to provide a catalyst which is impregnated with from about 0.1 to 8 wt % elemental phosphorus based upon the total weight of the impregnated mordenite catalyst. The products can be isolated by conventional techniques such as distillation.

25 Claims, No Drawings

PRODUCTION OF NONCYCLIC POLYALKYLENE POLYAMINES

TECHNICAL FIELD

This invention relates to a process for producing noncyclic polyalkylene polyamines by reacting one or more alkyleneamines in the presence of a catalyst.

BACKGROUND OF THE INVENTION

Alkylene polyamines such as ethylenediamine are used in a wide variety of applications. For example, ethylenediamine has wide utility and is used in the manufacture of chelating agents, surfactants, fabric softeners, lubricating oil additives, rubber accelerators, fungicides, insecticides, synthetic waxes, asphalt wetting agents and resinous polymers.

Highly acidic catalysts such as reductive metal catalysts have been employed in the production of alkyleneamines. However, such acidic catalysts are often non-selective for alcohol/amine reactions yielding a product mixture which also contains the corresponding ether, unsaturated hydrocarbon, polymeric hydrocarbon and other by-products.

Certain acidic phosphorus-containing catalysts are known to agglomerate and leach from the catalyst under standard liquid phase reaction conditions. Moreover, the use of reductive metal catalysts is not entirely satisfactory because the reaction involves high pressures, often greater than 1500 psi, and large molar ratios, typically greater than 5:1 of ammonia to alkanolamine. Consequently, a need exists to develop highly active and/or selective catalysts for producing alkylene polyamines, including polyalkylene polyamines.

British Patent 1,508,460 discloses a process for making diethylene triamine and/or triethylenetetramine by disproportionation of ethylenediamine. The conversion of ethylenediamine is carried out over a catalyst containing at least one transition metal selected from Group 8 of the Periodic Table of the Elements. The reaction is conducted at temperatures ranging from about 100° to 150° C. in the presence of hydrogen gas. The reaction is taken to a degree of conversion of 70% or less and does not form form linear products larger than triethylenetetramine.

U.S. Pat. No. 4,036,881 discloses a process for selectively preparing predominantly noncyclic polyalkylene polyamines wherein an alkylenediamine is contacted with an alkanolamine in the presence of a catalytically effective amount of a phosphorus-containing substance at a temperature of 250° C. to about 350° C. under a pressure sufficient to maintain the mixture essentially in the liquid phase. Suitable phosphorus-containing substances include acidic metal phosphates, phosphoric acid compounds and their anhydrides, phosphorous acid compounds and their anhydrides and the like.

U.S. Pat. No. 4,313,003 discloses a process for disproportionating monomethylamine to dimethylamine and ammonia wherein monomethylamine is passed over various catalysts including mordenite wherein the primary cation is Na, HNa having at least 2% Na, Mg, Ca, Ba at a temperature of 250° to 475° C. and a pressure of 7 to 7,000 kPa at a feed rate of 0.1 to 10 g of monomethylamine/g catalyst per hour, at a monomethylamine conversion of 15 to 75%.

U.S. Pat. No. 4,394,524 discloses a process for preparing noncyclic polyalkylene polyamines wherein ammonia, an alkylene polyamine and an alkanolamine are reacted in the presence of an effective amount of a phosphorus-containing substance or a salt of a sulfur-containing substance or its corresponding acid. The reaction is conducted at a temperature from about 200° to 350° C. under a pressure sufficient to maintain the reaction mixture essentially in the liquid phase. Suitable phosphorus-containing materials are enumerated in U.S. Pat. No. 4,036,881, which is discussed herein.

U.S. Pat. No. 4,503,253 discloses a process for preparing predominantly noncyclic polyalkylene polyamines wherein (1) an alkanolamine and (2) either ammonia, an alkyleneamine, or a primary or secondary amine are reacted in the presence of a catalyst. Suitable catalysts include phosphoric acid which is incorporated onto an inert support. The reaction is conducted at a temperature from about 175° to 400° C. under a pressure sufficient to maintain a substantial amount of the ammonia or amine in the reaction zone. Inert supports which can be utilized include silica, alumina carbon silica-alumina clays and molecular sieves such as aluminosilicates.

U.S. Pat. No. 4,547,591 discloses a process for preparing predominantly linear polyethylenepolyamines wherein ethylenediamine and an alkanolamine are reacted at a temperature ranging from 250° C. to about 400° C. and a pressure ranging from 500 to about 5000 psig in the presence of about 0.01 to about 20.0 weight percent of a silica-alumina catalyst and about 0.1 to about 3.0 weight percent of a phosphorus acid co-catalyst.

U.S. Pat. No. 4,578,517 discloses a process for preparing polyalkylene polyamines wherein ammonia or a primary or secondary amine and an alkanolamine compound are reacted in the presence of an effective amount of a Group IIIB metal acid phosphate at a temperature from about 175° to 400° C. under a pressure sufficient to maintain a substantial amount of the ammonia or amine in the reaction zone.

SUMMARY OF THE INVENTION

This invention relates to a process for selectively preparing predominantly noncyclic polyalkylene polyamines via a disproportionation reaction wherein one or more linear alkyleneamines are reacted in the presence of a mordenite catalyst. The term mordenite is meant to include those synthetic and naturally occurring zeolites having the mordenite topology as included under the general IUPAC structure code of mordenite (MOR). The mordenite catalysts of the present invention preferably possess a silicon to aluminum ratio of greater than 4.5.

In a preferred embodiment, the mordenite catalysts of the present invention are treated with an amount of a phosphorus-containing moiety sufficient to provide a catalyst which is impregnated with from about 0.01 to 15 wt % elemental phosphorus based upon the total weight of the impregnated mordenite catalyst.

Suitable phosphorus-containing moieties for impregnating the mordenite catalyst include, by way of example, ammonium dihydrogen phosphate, diammonium hydrogen phosphate, phosphoric acid, trimethyl phosphate and metal phosphates belonging to Groups 2 A/B, 3A/B, 4A/B and 8 of the Periodic Table of the Elements.

Suitable alkyleneamines for practicing the invention are represented by the formula:

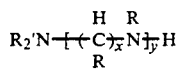

wherein R is independently selected from hydrogen, or a straight chain or branched $C_1$–$C_4$ alkyl group; R' is independently selected from hydrogen or a straight chain or branched $C_1$–$C_4$ alkyl group; x is an integer from 2 to 6, inclusive; and y is an integer from 1 to 4, inclusive.

The catalysts are typically activated prior to use in the process by a thermal or hydrothermal treatment. Base mordenite or phosphorus impregnated mordenite can be hydrothermally treated under an inert atmosphere by heating at temperatures ranging from about ambient to 800° C. in the presence of steam for about 0.5 to 48 hours prior to reacting the reactants in the presence of the catalyst. Alternatively, the mordenite and phosphorus impregnated mordenite catalyst can be thermally treated under an inert atmosphere by heating at temperatures ranging from about 90° to 800° C. for about 0.5 to 48 hours prior to reacting the reactants in the presence of the catalyst.

In a particular embodiment, diethylenetriamine (DETA), triethylenetetramine (TETA) and tetraethylenepentamine (TEPA) are selectively produced by contacting ethylenediamine in the presence of LZ-M-8 mordenite catalyst which has been impregnated with an amount of ammonium dihydrogen phosphate sufficient to impregnate the catalyst with from about 0.1 to 8 wt % phosphorus based upon the total weight of the impregnated mordenite catalyst.

The process can be carried out under batch conditions at temperatures ranging from about 150° to 400° C. and a pressure between about 1 and 300 atmospheres. Alternatively, the reaction can be carried out under fixed bed conditions using temperatures ranging from about 150° to 400° C., a pressure between about 1 to 300 atmospheres and a weight hourly space velocity (WHSV) of about 0.01 to 10 hr$^{-1}$. WHSV is defined as the mass of alkyleneamine feed per hour per mass of catalyst.

The present process is highly selective toward production of linear polyalkylene polyamines. An additional advantage of the present invention resides in the substantial reduction in reaction by-products such as cyclic products and water formed during known processes. The impregnated mordenite catalysts resist significant deactivation due to phosphate leaching. Moreover, the process is capable of producing higher polyalkylene polyamines such as triethylenetetramine and tetraethylenepentamine.

DETAILED DESCRIPTION OF THE INVENTION

The present invention pertains to a process for producing noncyclic polyalkylene polyamines in high conversion wherein at least one alkyleneamine is reacted in the presence of a mordenite catalyst. The present process is highly selective toward production of linear alkylene polyamines. An additional advantage of the present invention resides in the substantial reduction in reaction by-products such as cyclic products and water formed during processes known in the art. Moreover, the process is capable of producing higher polyalkylene polyamines such as triethylenetetramine and tetraethylenepentamine.

The term mordenite is meant to include those synthetic and naturally occurring zeolites having the mordenite topology as included under the general IUPAC structure code of mordenite (MOR). Due to mordenite's unidimensional pore structure, small amounts of impurities can exert enormous effects on adsorption rates and capacities. While naturally occurring mordenites vary widely in purity, the synthetic zeolites tend to have higher purity and controlled pore structure thereby rendering the synthetic mordenites better suited for catalytic applications. The preferred mordenite catalysts suitable for practicing this invention have a silicon to aluminum ratio of greater than about 4.5.

Mordenite can be synthesized from a wide variety of starting materials of both chemical and natural origins. Synthetic mordenites are typically produced with Si/Al ratios ranging from about 4.5 to 12.5. Mordenite is a porous crystalline catalyst having a rigid three-dimensional anionic network with intracrystalline channels whose narrowest cross section has essentially a uniform diameter. Mordenite is distinguished over crystalline alumino-silicate clays such as bentonite which have a two-dimensional layered structure and over amorphous catalysts such as alumino-silicates.

The catalytic activity and stability of mordenite catalysts can be enhanced by incorporating metals into the catalyst. This procedure is accomplished by contacting the ammonium form of mordenite with a solution of a salt of the desired metal. The metal will be incorporated by ion exchange into the mordenite catalyst when the metal is in the form of a cation. All or part of the ammonium ions can be replaced by the metal cations. When the metal is in the form of an anionic moiety or a neutral species, the metal is impregnated onto the catalyst. After the metal has been incorporated into the ammonium form of mordenite, the catalyst is dried. Base catalysts suitable for practicing this invention include mordenites which have been ion exchanged with cations such as Al, Na, H, K, Ca, Sr and the rare earth metals prior to, or following impregnation with a phosphorus-containing moiety. Furthermore, prior to or after impregnating the subject catalysts with a phosphorus-containing moiety, the mordenite catalyst can be dealuminated to the extent desired by methods well known in the art.

In a preferred embodiment, LZ-M-8 mordenite catalyst is utilized. LZ-M-8, which is commercially available from Union Carbide Corporation, is a low sodium, partially dealuminated, ammonium ion exchanged mordenite. Thermal treatment of LZ-M-8 drives off the ammonia creating the strong acid, catalytically active hydrogen form. Moreover, the LZ-M-8 catalyst has high acid stability and resists thermal degradation to over 900° C. For purposes of illustration, LZ-M-8 has the following chemical composition (wt % anhydrous).

| | |
|---|---|
| $SiO_2$ | 86.1 |
| $Al_2O_3$ | 8.6 |
| $Na_2O$ | 0.05 |
| $(NH_4)_2O$ | 4.4 |
| $SiO_2/Al_2O_3$ (molar ratio) | 17.0 |
| $Na_2O/Al_2O_3$ (molar ratio) | 0.01 |

Another embodiment of the invention relates to a process for making noncyclic polyalkylene polyamines wherein the disclosed mordenite catalysts are treated with an amount of a phosphorus-containing moiety sufficient to provide a catalyst which is impregnated with from about 0.01 to 15 wt %, preferably about 0.1 to 8 wt %, elemental phosphorus based on the total weight of the impregnated mordenite catalyst.

Utilization of phosphorus impregnated mordenite catalysts in the preparation of noncyclic polyalkylene polyamines provides several improvements over catalysts known in the art. The impregnated mordenite catalysts are unexpectedly more active and selective than the base mordenite prepared in the absence of impregnation with a phosphorus-containing moiety. The instant process also provides a one-step process for preparing higher polyalkylene polyamines such as triethylenetetramine and tetraethylenepentamine.

The alkyleneamine reactants which can be used in practicing the process are represented by the general formula:

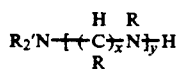

wherein each R is independently selected from hydrogen or a straight chain or branched $C_1$-$C_4$ alkyl group; R' is independently selected from hydrogen or a straight chain or branched $C_1$-$C_4$ alkyl group; x is an integer from 2 to 6, inclusive; and y is an integer from 1 to 4, inclusive. When reference is made to the term alkyl, the invention contemplates use of primary, secondary and tertiary substituents. When a branched alkyleneamine reactant is desired, R is preferably a methyl group. Suitable alkyl groups include methyl, ethyl and butyl, sec-butyl and tert-butyl and higher alkyls.

Examples of alkyleneamine reactants suitable for practicing the invention include propylenediamine, N-methylpropylenediamine, 1,2-propylenediamine, diethylenetriamine, N-methylethylenediamine, N,N-dimethylethylenediamine, N,N,N'-trimethyldiethylenetriamine, and substituted and unsubstituted triethylenetetramines and tetraethylenepentamines. The preferred alkyleneamine reactant is ethylenediamine.

The reactants suitable for practicing this invention can be a mixture of one or more alkyleneamines or a single alkyleneamine. When reference is made to alkyleneamines, the term shall be interpreted as encompassing both alkylene polyamines and polyalkylene polyamines. For example, ethylenediamine can be reacted with diethylenetriamine to produce a mixture of triethylenetetramine and higher polyalkylene polyamines.

The catalysts useful for practicing this invention include the base mordenites as defined herein and base mordenites which are impregnated with a phosphorus-containing moiety. Suitable phosphorus-containing moieties for impregnating the base mordenite catalysts include acidic metal phosphates, organic phosphates such as trimethyl phosphate and inorganic phosphates such as ammonium dihydrogen phosphate, diammonium hydrogen phosphate, phosphoric acid and their anhydrides, phosphorous acid compounds and their anhydrides, alkyl or aryl phosphate esters, alkyl or aryl phosphite esters, alkyl or aryl substituted phosphorous acids and phosphoric acids wherein the alkyl groups have from 1 to about 8 carbon atoms and the aryl groups have from about 6 to about 20 carbon atoms, alkali metal monosalts of phosphoric acid and mixtures of any of the above.

Specific examples of alkyl and aryl substituted phosphorous and phosphoric acids that may be used in accordance with the invention are phenylphosphinic, ethylphosphonic, phenylphosphonic, naphthaphosphonic and methylphosphinic acids. Examples of the alkyl and aryl substituted phosphorous and phosphoric acid esters are diethyl phenylphosphonate, dimethylphosphonate, methyl phenylphosphinate, ethyl naphthaphosphinate, and dipropyl methylphosphonate.

More particularly, suitable metal phosphates and metal acid phosphates include metal phosphates or metal acid phosphates of metals belonging to Groups 2 A/B, 3A/B, 4A/B or 8 of the Periodic Table of the Elements (e.g., aluminum phosphate, boron phosphate, lanthanum hydrogen phosphate, strontium hydrogen phosphate).

Suitable phosphoric acid compounds include aqueous or anhydrous phosphoric acids such as orthophosphoric acid, pyrophosphoric acid, metaphosphoric acid, and condensed phosphoric acids such as polyphosphoric acids.

In addition, any commercially available mono-, di- or trialkyl or aryl phosphate or phosphine ester can be employed as the catalyst in the inventive process. Additionally, bis(phosphates) and secondary phosphate esters such as those disclosed in U.S. Pat. Nos. 3,869,526 and 3,689,527, respectively, can be used. Preferably, the lower alkyl esters are employed such as those having from 1 to about 8 carbon atoms per alkyl group. Preferred aryl esters contain from about 6 to about 20 carbon atoms and may include a phenyl group or alkyl-substituted phenyl group.

The amount of phosphorus-containing moiety to be impregnated onto the mordenite catalyst is that amount which is sufficient to achieve the desired selectivity and conversion to the desired product. Generally the amount of phosphorus-containing moiety impregnated onto the mordenite catalyst ranges from about 0.01 to 15 wt % and preferably between about 0.1 and 8 wt %, based upon the total weight of the impregnated mordenite catalyst. However, the level of impregnation should not be such substantially all of the pores on the mordenite catalyst become clogged thereby rendering the catalyst inactive for the desired reaction.

The quantity of phosphorus-containing moiety to be impregnated onto the mordenite catalyst will also vary depending upon the reactivity of the catalyst and the reactivity of the reactants. An effective amount of catalyst is used, i.e., that amount which causes a reaction involving one or more linear alkyleneamines to selectively produce the desired noncyclic polyalkylene polyamine at suitable conversion at the temperature and pressures used. For a batch reaction, an effective amount of catalyst typically ranges from about 0.1 to 25 wt % based upon the total amount of alkyleneamines present in the reaction mixture, and preferably is an amount of about 0.1 to 10.0 wt %. Within these ranges though, the level of catalyst is somewhat empirical and is adjusted depending on the product desired.

In the preparation of noncyclic polyalkylene polyamines, the process is typically run at temperatures ranging from about 150° to 400° C. and pressures between about 1 and 300 atmospheres. More particularly, the process can be advantageously run under batch conditions at temperatues ranging from about 150° and 400° C. and under pressures ranging from between about 1 and 300 atmospheres. Reaction conditions for carrying out the process under fixed bed conditions require temperatures ranging from about 150° to 400° C., pressure ranging from about 1 to 300 atmospheres and a weight hourly space velocity of about 0.01 to 10 hr$^{-1}$. The preferred temperature depends upon the rate of reaction desired to produce the noncyclic polyalkylene polyamines. Recovery of the polyalkylene polyamines can be accomplished by conventional techniques including distillation.

In a preferred embodiment, diethylenetriamine is produced by disproportionating ethylenediamine in the presence of a mordenite catalyst which has been impregnated with 1.9 wt % elemental phosphorus to produce diethylenetriamine and ammonia. The reaction is conducted at temperatures ranging from about 150° to 400° C. and a pressure ranging from about 1 to 300 atmospheres for both continuous and batch reactions. Typical reaction times for batch reactions range from about 1 to 6 hours. Continuous fixed bed reactions can be advantageously run at a space velocity, expressed as weight hourly space velocity, (WHSV) ranging from about 0.01 to 10 hrs$^{-1}$ (based on ethylenediamine feed).

Preferably, the base mordenite and phosphorus impregnated mordenite catalysts of the present invention are subjected to a hydrothermal or thermal treatment prior to use in the process although such treatment is not required to practice the invention. The hydrothermal and thermal treatments may be conducted in the reactor prior to contacting the reactants with the catalyst or as a separate step. The catalyst is typically introduced into a reactor and heated above ambient temperature, preferably between about 80° and 150° C., while under a helium atmosphere of about 1 to 220 atmospheres for a period ranging from about 0.5 to 12 hours to remove residual moisture. The catalyst may be dried during one or more time periods utilizing one or more discrete temperatures or temperature ramping. The amount of time and the temperature regime employed to dry the catalyst is not critical to the invention. The catalyst is heated to temperatures between about ambient and 800° C., preferably between about 90° and 200° C. in an inert atmosphere for a period ranging from about 0.5 to 48 hours. The catalyst is then heated to between about 200° and 800° C., preferably between about 450° and 550° C., in the presence of steam for a period of about 0.5 to 48 hours. The catalyst is cooled to between room temperature and reactor operating temperature, the water flow is discontinued and the catalyst is allowed to dry.

The catalysts of the present invention may optionally be subjected to a thermal treatment wherein the catalyst to be treated is heated to temperatures ranging from about ambient to 800° C. in an inert atmosphere for a period of about 0.5 to 48 hours. The preferred temperature for thermally treating the catalysts ranges from about 150° to 500° C.

The following examples are provided to further illustrate various embodiments and to provide a comparison between the base mordenite and impregnated mordenite catalysts of the present invention and other catalysts used in preparing diethylenetriamine and higher polyalkylene polyamines. The examples contained herein are not intended to restrict the scope of the invention.

EXAMPLE 1

Preparation of Base Mordenite Catalyst

H-mordenite powder, without binder, (LZ-M-8 from Union Carbide Corporation) was pelletized, crushed and sieved to yield 12/18 mesh particles. The catalyst was loaded into a 5/16" diameter, 24" long, stainless-steel reactor tube. Six grams of 12/18 mesh catalyst were placed between beds of 12/18 mesh quartz chips is the reactor tube. The reactor tube was placed in a tubular furnace with three heating zones where it was heated to achieve an isothermal temperature profile along the length of the catalyst bed. A helium purge at a rate of 1000 cc/min was maintained through the reactor tube during the temperature program. The catalyst was heated to 110° C. in 0.7 hours and maintained at this temperature for one hour to remove residual moisture. The catalyst was then heated to 200° C. in 0.7 hours and maintained at this temperature for 5 hours. After this period of time, the helium flow was reduced to 250 cc/min; and a water flow was started at a rate of 20 cc/hour. The pressure in the reactor tube was approximately 100 psi during the water treatment. The catalyst was heated to 500° C. in 1.5 hours and maintained at this temperature for 3.5 hours. The catalyst was then cooled to 105° C. At this time, the water was discontinued; and the helium flow was increased to 1000 cc/min. The catalyst was dried at 105° C. for 0.5 hours and then allowed to cool to room temperature before the reaction study began.

EXAMPLE 2

Phosphorus Impregnation of Mordenite Catalyst 25.0 grams of ammonium dihydrogen phosphate ($NH_4H_2PO_4$) were dissolved in 500 ml of distilled water. 112.0 grams of H-mordenite powder (LZ-M-8 from Union Carbide Corporation) without binder, were added to this solution and stirred for 30 hours. The solution was filtered, and the zeolite was recovered. The impregnated zeolite was air-dried in a ventilation hood for six days. The impregnated zeolite was later dried in a vacuum oven at 60° C. The resulting zeolite had an oxygen capacity of 21.4 grams $O_2$/100 grams sample at liquid nitrogen temperatures and the following composition by weight: 1.9% elemental phosphorus, 39.8% silicon, and 4.1% aluminum. This translates into approximately 4.4 wt % $P_2O_5$. The catalyst was pelletized, crushed and sieved to yield 12/18 mesh particles.

EXAMPLE 3

Hydrothermal Pretreatment of Phosphorous Impregnated Mordenite Catalysts

The catalyst prepared in Example 2 was loaded into a 5/16' diameter, 24" long stainless-steel reactor tube. Six grams of 12/18 mesh catalyst were placed between beds of 12/18 mesh quartz chips in the reactor tube. The reactor tube was placed in a tubular furnace with three heating zones and was heated to achieve an isothermal temperature profile along the length of the catalyst bed. A helium purge at a rate of 1000 cc/min was maintained through the reactor tube during the temperature program. The catalyst was heated to 100° C. in 0.7 hours and maintained at this temperature for one hour to remove residual moisture. The catalyst was then heated to 200° C. in 0.7 hours and maintained at this temperature for 15 hours. After this period of time, the helium flow was reduced to 250 cc/min; and a water flow was started at a rate of 20 cc/hour. After 30 minutes, the water flow was reduced to 10 cc/hour. The pressure in the reactor tube was approximately 100 psig during the water treatment. The catalyst was heated to 500° C. in 1.5 hours and maintained at this temperature for 3.5 hours. The catalyst was then cooled to 105° C. At this time the water was discontinued and the helium flow was increased to 1000 cc/min. The catalyst was dried at 105° C. for 17 hours and then allowed to cool to room temperature before the reaction study began.

EXAMPLE 4

Preparation of Hy Zeolite

LZ-Y82 powder, without binder, from Union Carbide Corporation was pelletized, crushed and sieved to yield 12/18 mesh particles. Six grams of the 12/18 mesh zeolite were loaded into a 5/16" diameter, 24" long, stainless steel reactor tube. The reactor tube was placed in a tubular furnace with three heating zones, where it was heated to achieve an isothermal temperature profile along the length of the catalyst bed during the reaction study.

EXAMPLE 5

Use of Catalysts

The packed catalyst tube and furnace employed in Examples 1, 3 and 4 were used for the disproportionation of ethylenediamine. The reaction were run under the same reaction conditions (311° C., 820 psi). Conversions and selectivities were determined by gas chromatography of the reactor effluent.

The results for the disproportionation of ethylenediamine over catalysts of Examples 1–4 to form linear polyamines are reported in Table 1. Runs 1 through 3 demonstrate that the disproportionation of ethylenediamine over LZ-M-8 provides a selectivity to linear products ranging from 52% to 76%. In contrast, Runs 4 and 5 illustrate that LZ-Y-82 provides poor selectivity, ranging from 1 to about 7% selectivity to linear products. The linear product, pentaethylenehexamine, was identified in the chromatogram in the mordenite runs, but a quantitative analysis of the product was not determined. Therefore, pentaethylenehexamine is included in the unknowns.

Runs 1 and 2 demonstrate that while the impregnated mordenite is not as active as the base mordenite catalyst (comparing conversions at WHSV=0.6), the selectivity to linear products is much higher for the phosphorus impregnated mordenite catalyst than the base mordenite catalyst. For example, the phosphorus impregnated mordenite catalyst (Run 2) is 60% selective toward production of DETA while LZ-M-8 (Run 1) and LZ-Y-82 (Run 4) demonstrate DETA selectivity of 32% and 5%, respectively. As a second basis of comparison, the amount of unknowns formed with the 4.4% $P_2O_5$/LZ-M-8 (Run 3) is 24% whereas the LZ-Y-82 catalyst (Run 5) yielded about 65% unknowns and only 7% linear products.

TABLE 1

CATALYTIC DISPROPORTIONATION OF ETHYLENEDIAMINE AT T = 311° C., P = 820 PSIG

| Run | Catalyst (Example) | WHSV (HR$^{-1}$) | Conversion % | DETA | TETA | Selectivity (Wt %)* TEPA | Linear | Cyclic | Unknowns** |
|---|---|---|---|---|---|---|---|---|---|
| 1 | LZ-M-8 (1) | 0.6 | 71.5 | 31.9 | 13.8 | 7.2 | 52.9 | 9.2 | 35.3 |
| 2 | LZ-M-8 (3) 4.4% $P_2O_5$ | 0.6 | 53.1 | 59.5 | 13.7 | 2.5 | 75.7 | 1.8 | 20.6 |
| 3 | LZ-M-8 (3) 4.4% $P_2O_5$ | 0.36 | 62.5 | 48.4 | 16.6 | 6.1 | 71.1 | 3.0 | 23.9 |
| 4 | LZ-Y-82 (4) | 0.6 | 94.0 | 0.5 | 0.2 | 0.2 | 0.9 | 11.5 | 87.1 |
| 5 | LZ-Y-82 (4) | 1.5 | 72.7 | 5.0 | 1.3 | 0.2 | 6.5 | 26.0 | 65.0 |

WHSV = Grams of ethylenediamine per hour per grams of catalyst.
DETA = Diethylenetriamine
TETA = Triethylenetetramine
TEPA = Tetraethylenepentamine
*reactant free, water free, ammonia free, effluent composition
**refers to compounds not identified Comparison of Runs 1 and 5 demonstrates that while both LZ-M-8 and LZ-Y82 show similar conversion of ethylenediamine at the same WHSV, the selectivity to linear amines for LZ-M-8 is much greater than that achieved by LZ-Y82 (53% vs. 6.5%). Furthermore, the use of LZ-M-8 results in a substantial decrease in undesirable unknowns compared to the reaction utilizing LZ-Y82 (35.3% vs. 65%). These results demonstrate that the mordenite catalysts of this invention provide superior selectivity to the desired disproportionation products than other zeolite catalysts such as Y zeolites.

As previously stated, this invention relates to a process for selectively preparing predominantly noncyclic alkylene polyamines wherein one or more linear alkyleneamines are reacted in the presence of a mordenite catalyst. For example disproportionation of diethylenetriamine (DETA) over hydrothermally treated LZ-M-8 which has been impregnated with 1.9 wt % elemental phosphorus under reaction conditions similar to Example 5 showed about 15 wt % selectivity to linear triethylenetetramine (TETA), 25 wt % selectivity to linear tetraethylenepentamine (TEPA) and approximately 30 wt % selectivity to cyclic products, primarily piperazine. The phosphorus impregnated catalyst showed no signs of catalyst deactivation after 200 hours on stream, the first 150 hours of which utilized a 1:1 ratio of DETA to water.

The invention also contemplates the reacting of two or more linear alkyleneamines. For example, the reaction of a 2:1 molar ratio of ethylenediamine and diethylenetriamine in the presence of a hydrothermally treated mordenite catalyst under conditions similar to Example 5 results in improved selectivities to non-cyclic TETAs and TEPAS. At EDA and DETA conversions of 57% and 14%, respectively, the reaction selectivity toward TETAs and TEPAs was 30% and 15% comprising 96% and 92% non-cyclic isomers, respectively.

Disproportionation of amines over phosphate impregnated mordenite provide a significant and unexpected improvement in selectivity to linear alkylene polyamine products compared to the non-phosphate-impregnated mordenite catalysts and other zeolite catalysts such as Y zeolites. Moreover, this process provides a convenient route to higher polyalkylene polyamines such as triethylenetetramine and tetraethylenepentamine.

We claim:

1. A process for producing noncyclic polyalkylene polyamines which comprises: reacting at least one alkyleneamine in the presence of a mordenite catalyst under conditions sufficient to effect a disproportionation reaction and recovering the polyalkylene polyamine.

2. The process according to claim 1 wherein the alkyleneamine is ethylenediamine.

3. The process according to claim 1 wherein the alkyleneamine is diethylenetriamine.

4. The process according to claim 1 wherein the alkyleneamine is a mixture of ethylenediamine and diethylenetriamine.

5. The process according to claim 1 wherein said mordenite catalyst is LZ-M-8.

6. The process according to claim 1 wherein the mordenite catalyst is treated with an amount of a phosphorus-containing moiety sufficient to impregnate the catalyst with from about 0.01 to 15% elemental phosphorus based upon the total weight of the impregnated mordenite catalyst prior to reacting the alkyleneamine in the presence of the catalyst.

7. The process according to claim 6 wherein said phosphorus-containing moeity is selected from the group consisting of ammonium dihydrogen phosphate, diammonium hydrogen phosphate, phosphoric acid, trimethyl phosphate and metal phosphates belonging to Groups 2 A/B, 3 A/B, 4 A/B and 8 of the Periodic Table of the Elements.

8. A process for producing noncyclic polyalkylene polyamines which comprises: reacting at least one alkyleneamine represented by the formula:

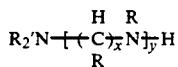

wherein each R is independently selected from hydrogen or a straight chain or branched $C_1$-$C_4$ alkyl group; R' is hydrogen or a straight chain or branched $C_1$-$C_4$ alkyl group; x is an integer from 2 to 6, inclusive; and y is an integer from 1 to 4, inclusive, in the presence of a mordenite catalyst under conditions sufficient to effect a disproportionation reaction and recovering the polyalkylene polyamine.

9. The process according to claim 8 wherein the mordenite catalyst is treated with an amount of a phosphorus-containing moiety sufficient to impregnate the catalyst with from about 0.01 to 15% elemental phosphorus based upon the total weight of the impregnated mordenite catalyst prior to reacting the compound in the presence of the catalyst.

10. The process according to claim 9 wherein the impregnated catalyst is hydrothermally treated under an inert atmosphere by heating at temperatures ranging from about ambient to 800° C. for a period ranging from about 0.5 to 48 hours followed by heating the catalyst to temperatures ranging from about 200° C. to 800° C. in the presence of steam for a period ranging from about 0.5 to 48 hours prior to reacting the alkyleneamine in the presence of the catalyst.

11. The process according to claim 9 wherein the impregnated catalyst is thermally treated under an inert atmosphere at temperatures ranging from about 150° to 500° C. for about 0.5 to 48 hours prior to reacting the alkyleneamine in the presence of the catalyst.

12. The process according to claim 6 wherein said alkyleneamine is selected from the group consisting of N-methylpropylenediamine, 1,2-propylenediamine, diethylenetriamine, N-methylethylenediamine, N,N-dimethylethylenediamine, N,N,N'-trimethyldiethylenetriamine, and substituted and unsubstituted triethylenetetramines and tetraethylenepentamines.

13. The process according to claim 9 wherein said mordenite catalyst is LZ-M-8.

14. The process according to claim 7 wherein said source of phosphorus-containing moiety is selected from the group consisting of ammonium dihydrogen phosphate, diammonium hydrogen phosphate, phosphoric acid, trimethyl phosphate and metal phosphates belonging to Groups 2 A/B, 3A/B, 4A/B and 8 of the Periodic Table of the Elements.

15. The process according to claim 14 wherein said metal phosphate is selected from the group consisting of aluminum phosphate, boron phosphate, lanthanum hydrogen phosphate and strontium hydrogen phosphate.

16. The process according to claim 13 wherein the reacting is carried out under batch conditions at temperatures ranging from about 150° to 400° C. and a pressure between about 1 and 300 atmospheres.

17. The process according to claim 13 wherein the reacting is carried out under fixed bed conditions at temperatures ranging from about 150° and 400° C., a pressure of between about 1 and 300 atmospheres and a weight hourly space velocity of about 0.01 to 10 hr.$^{-1}$.

18. A process for producing diethylenetriamine which comprises: reacting ethylenediamine in the presence of a mordenite catalyst under conditions sufficient to effect a disproportionation reaction and recovering the diethylenetriamine.

19. The process according to claim 18 wherein the mordenite catalyst is treated with an amount of a phosphorus-containing moiety sufficient to impregnate the catalyst with from about 0.1 to 8 wt % elemental phosphorus based upon the total weight of the impregnated mordenite catalyst prior to reacting the alkyleneamine in the presence of the catalyst.

20. The process according to claim 19 wherein said mordenite catalyst is LZ-M-8.

21. The process according to claim 20 where said phosphorus-containing moiety is ammonium dihydrogen phosphate.

22. The process according to claim 21 wherein the impregnated catalyst is thermally treated under an inert atmosphere at temperatures ranging from about 150° to 500° C. for about 0.5 to 48 hours prior to reacting the alkyleneamine in the presence of the catalyst.

23. The process according to claim 21 wherein the impregnated catalyst is hydrothermally treated under an inert atmosphere by heating at temperatures ranging from about 90° to 200° C. for a period ranging from about 0.5 to 48 hours followed by heating the catalyst to temperatures ranging from about 450° to 550° C. in the presence of water for a period of about 0.5 to 48 hours prior to reacting the alkyleneamine in the presence of the catalyst.

24. The process according to claim 23 wherein the reacting is carried out under batch conditions at temperatures ranging from about 150° to 400° C. and a pressure between about 1 and 300 atmospheres.

25. The process according to claim 23 wherein the reacting is carried out under fixed bed conditions at temperatures ranging from about 150°-400° C., a pressure between about 1 and 300 atmospheres and an weight hourly space velocity of about 0.01 to 10 hr.$^{-1}$.

* * * * *